Figure 1:
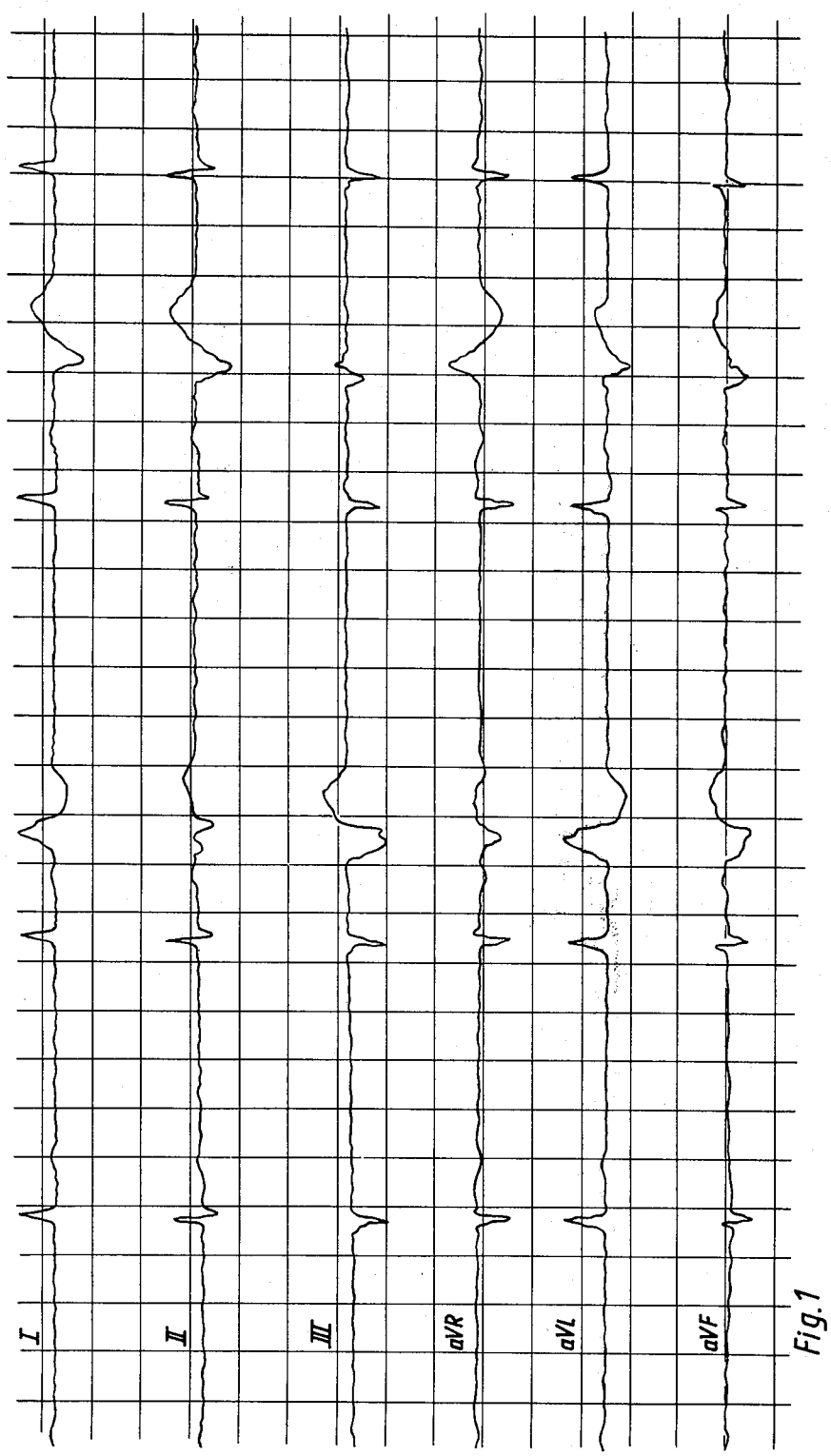

United States Patent [19]

Bickel

[11] 3,968,205

[45] July 6, 1976

[54] INFUSION SOLUTION FOR THE TREATMENT OF TACHYCARDIAC DISTURBANCES OF HEART RHYTHM AND USE THEREOF

[75] Inventor: Johanna Bickel, Nurnberg, Germany

[73] Assignee: J. Pfrimmer and Co., Erlangen, Germany

[22] Filed: Jan. 23, 1975

[21] Appl. No.: 543,456

[30] Foreign Application Priority Data

Jan. 31, 1975 Germany............................ 2404620

[52] U.S. Cl................................ 424/153; 424/127; 424/154; 424/324
[51] Int. Cl.² ................. A61K 33/14; A61K 33/00; A61K 33/06; A61K 31/165
[58] Field of Search ............ 424/153, 154, 127, 324

[56] References Cited

OTHER PUBLICATIONS

Penna et al., Chem. Abst., vol. 61 (1964), p. 12486b.
Guidicelli et al., Chem. Abst., vol. 80 (1974), p. 66656b.
Grollman, Pharmacology and Therapeutics, 6th edition (1965), p. 1004.

*Primary Examiner*—Sam Rosen
*Attorney, Agent, or Firm*—Burns, Doane, Swecker & Mathis

[57] ABSTRACT

An improved lidocaine-containing infusion solution for the treatment of tachycardiac disturbances of heart rhythm is disclosed. The improved solution contains an antiarrhythmic effective amount of potassium and magnesium ions.

4 Claims, 2 Drawing Figures

INFUSION SOLUTION FOR THE TREATMENT OF TACHYCARDIAC DISTURBANCES OF HEART RHYTHM AND USE THEREOF

At the present time, lidocaine (alpha-diethylaminoaceto-2, 6-xylidide, $C_{14}H_{22}N_2O$) is injected intravenously for the treatment of ventricular tachycardia (an arrythmia of the heart). Since this administration by injection achieves only a short effective duration of less than 1 hour, a long time treatment is not possible. A further disadvantage of the treatment by injection is that immediately after the injection a high lidocaine concentration peak occurs which represents a risk in the case of repeated injections due to the toxicity of lidocaine. The addition of lidocaine to other infusion solutions is also known. This addition treatment, however, is cumbersome and risky.

According to the present invention, a new infusion solution has been prepared in which lidocaine is used in combination with potassium and magnesium ions present in certain quantities. Additives presently utilized with lidocaine infusion solutions (e.g., sodium chloride, glucose and the like) may also be present. According to the present invention, the intravenously administerable infusion solution for the treatment of ventricular tachycardia contains, beside the customary additives, 0.5–5 g/l of lidocaine 20–100 milliequivalents (mVal) per liter of potassium and 10–60 milliequivalents (mVal) per liter of magnesium. The potassium and magnesium may be added to the solution in any physiologically compatible manner.

As a result of the new combination of lidocaine with potassium and magnesium in the amounts indicated, the effects realized during long time infusion administration are superior to those achieved presently. Surprisingly, it was found that these advantages do not merely occur as a result of the useable lidocaine-infusion solution. Rather, as a result of the addition of potassium and magnesium ions according to the invention, a considerable higher antiarrhythmic effectiveness occurs. The surprising evidence of the increased protection against arrhythmia is achieved even in the case of a body having a serum-potassium concentration lying moderately above the standard. The improved lidocaine solution of the present invention may be utilized in the same manner as lidocaine solutions presently are used.

The invention is additionally illustrated in connection with the following Example which is to be considered as illustrative of the present invention. It should be understood, however, that the invention is not limited to the specific details of the Example.

EXAMPLE

An aqueous infusion solution according to the invention contains the following:

| | | | | |
|---|---|---|---|---|
| Sodium | ions | 60 | milliequivalents | (mVal)/liter |
| potassium | ions | 60 | " | |
| magnesium | " | 20 | " | |
| chloride | " | 70 | " | |
| acetate | " | 40 | " | |
| Malate | " | 20 | " | |
| phosphate | " | 10 | " | |
| glucose | | 30 | grams/liter | |
| sorbitol | | 35 | " | |
| xylitol | | 35 | " | |
| Lidocaine | | 2000 | milligrams/liter | |

This solution is easily produced in a conventional manner to form a sterile solution ready to use and free of pyrogen.

Its surprising compatibility and effectiveness are proven by the following experiments described and confirmed in clinical tests. Pharmacological examinations have shown that as a result of the use of the new infusion solution of the present invention, the aconitine arrhythmia in rat hearts have been influenced favorably in situ. Two hours after infusion of the test solution of the Example, 37.5 µg of arrhythmia producing acontine could be added per kg of rat before the first extrasystoles occurred. In comparative experiments on similar rats utilizing the same amount of lidocaine in a physiological sodium chloride solution, the first extrasystoles occurred in the case of aconitine doses of 27.14 µg per/kg of rat 2 hours after the lidocaine infusion. From these tests it is obvious that the effect of the lidocaine protection against arrhythmia is thus increased by a simultaneous administration of potassium and magnesium. The difference is significant at $p<0.05$.

Since the serum-potassium concentration in the above experiment amounted to $5.98 \pm 0.55$ milliequivalents/liter (mVal/l) ($n = 10$), this experiment at the same time also shows the strong antiarrhythmic protection obtained when the serum-potassium concentration is above the standard.

Also the electric fibrillation threshold of cat hearts in situ is favorably influenced. After 6 hours of lidocaine infusion, the strength of the stimulating current could be increased by 56% of the starting value for the production of a ventricular fibrillation in a cat heart. After the infusion of the solution of the Example, which contains lidocaine as well as potassium and magnesium ions, the ventricular fibrillation wave was achieved only by increasing the stimulating current to 140% of its starting value. The effect of the lidocaine increasing the ventricular fibrillation threshold is thus also considerably increased by the simultaneous administration of potassium and magnesium ions with the lidocaine.

Figure 2:
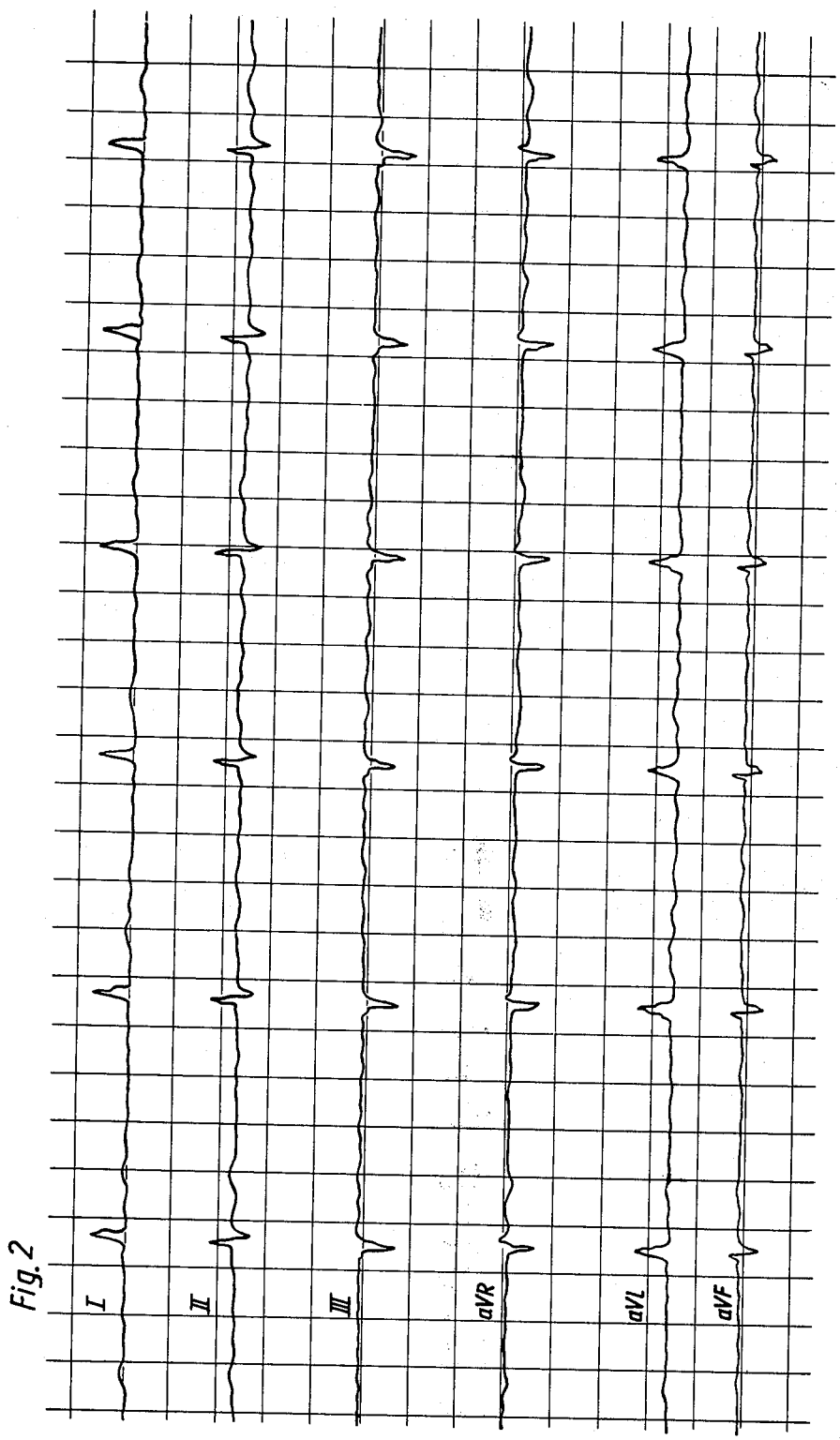

The infusion solution of the invention was tested clinically and showed perfect compatibility with human patients. The good antiarrhythmic effect of the lidocaine solution of the present invention was proven in the case of patients with clear arrhythmia in their electrocardiogram as may be seen by comparing FIG. 1 which is an illustration of the electrocardiogram recording obtained from a patient suffering arrhythmia with FIG. 2 which is a similar illustration of his electrocardiogram recording obtained 8 hours after the start of infusion with the lidocaine solution of the present invention.

It is clear that the administration of the solution of the present invention represents considerable progress in the therapy of ventricular tachycardia.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed:

1. An infusion solution for the treatment of ventricular tachycardia comprising an effective amount of lidocaine and an antiarrhythmic effective amount of potassium and magnesium ions.

2. The infusion solution of claim 1, wherein the infusion solution contains from about 0.5 to 5 grams per liter of lidocaine, 20 to 100 milliequivalents per liter of potassium ions and 10 to 60 milliequivalents magnesium ions.

3. A method of treating ventricular tachycardia which comprises administering an effective amount of the infusion solution of claim 1.

4. A method of treating ventricular tachycardia which comprises administering an effective amount of the infusion solution of claim 2.

* * * * *